United States Patent [19]

Benedikter et al.

[11] 4,259,342
[45] Mar. 31, 1981

[54] ANTIANGINAL TREATMENT WITH AZEPINE DERIVATIVES

[75] Inventors: Lothar Benedikter, Biberach an der Riss, Fed. Rep. of Germany; Walter Kobinger; Ludwig Pichler, both of Vienna, Austria; Hanns Ihrig; Gerhart Griss, both of Biberach an der Riss, Fed. Rep. of Germany

[73] Assignee: Boehringer Ingelheim GmbH, Ingelheim am Rhein, Fed. Rep. of Germany

[21] Appl. No.: 37,747

[22] Filed: May 10, 1979

[30] Foreign Application Priority Data

May 12, 1978 [DE] Fed. Rep. of Germany ....... 2820808

[51] Int. Cl.³ .................... A61K 31/42; A61K 31/425
[52] U.S. Cl. ..................................... 424/270; 424/272
[58] Field of Search ................................ 424/270, 272

[56] References Cited

U.S. PATENT DOCUMENTS 3,804,849   4/1974   Griss et al. ........................... 424/270
3,907,996   9/1975   Griss et al. ..................... 424/270;272

OTHER PUBLICATIONS

Goodman et al.,The Pharmacological Basis of Therapeutics, The MacMillan Co., N.Y., 3rd Ed., 1965, pp. 563-565, 736-751.

The Merck Manual, Merck & Co., Rahway, N.J., 12th Ed., 1972, pp. 371-375.

Primary Examiner—Anna P. Fagelson
Attorney, Agent, or Firm—Hammond & Littell, Weissenberger & Muserlian

[57] ABSTRACT

Antianginal pharmaceutical compositions containing as the active ingredient a compound of the formula

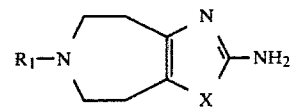

wherein
  $R_1$ is hydrogen, unsubstituted or hydroxyl-substituted alkyl of 1 to 4 carbon atoms; allyl; or unsubstituted or halo-, methyl-, methoxy- or trifluoromethyl-substituted benzyl; and
  X is oxygen or sulfur;
or a non-toxic, pharmaceutically acceptable acid addition salt thereof; and methods of treating angina pectoris therewith.

3 Claims, No Drawings

ANTIANGINAL TREATMENT WITH AZEPINE DERIVATIVES

This invention relates to novel antianginal pharmaceutical compositions containing as an active ingredient a 2-amino-4,5,7,8-tetrahydro-6H-oxazolo or thiazolo[5,4-d]azepine or a non-toxic acid addition salt thereof, as well as to a method of using the same for the treatment of anginal disorders, especially angina pectoris.

THE PRIOR ART

Belgian Pat. No. 771,330 and U.S. Pat. Nos. 3,804,849 and 3,907,996 disclose, inter alia, azepine derivatives of the formula

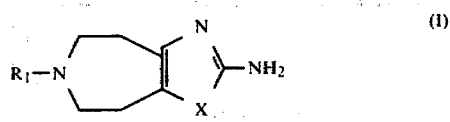

wherein
$R_1$ is hydrogen, unsubstituted or hydroxyl-substituted alkyl of 1 to 4 carbon atoms; allyl; or unsubstituted or halo-, methyl-, methoxy- or trifluoromethyl-substituted benzyl; and
X is oxygen or sulfur;
and non-toxic, pharmaceutically acceptable acid addition salts thereof.

These patents further disclose that the compounds of the formula I have useful pharmacodynamic properties. Thus, depending upon the meaning of $R_1$ and X, they particularly exhibit hypotensive, sedative, antitussive and/or antiphlogistic activities. More specifically, the azepine derivatives of the formula I wherein $R_1$ is alkyl of 1 to 4 carbon atoms, allyl, benzyl of halo-, methyl-, methoxy- or trifluoromethyl-substituted benzyl, and X is sulfur, exhibit primarily hypotensive activity; on the other hand, those wherein $R_1$ is hydrogen, unsubstituted or hydroxyl-substituted alkyl of 1 to 4 carbon atoms or allyl, and X is oxygen, exhibit primarily antitussive activity.

DESCRIPTION OF THE INVENTION

We have discovered that the azepine derivatives of the formula I above and their non-toxic, pharmaceutically acceptable acid addition salts also exhibit antianginal activity, and are therefore useful for the treatment of angina pectoris.

Preferred are those compounds of the formula I wherein $R_1$ is hydrogen, allyl, alkyl of 1 to 4 carbon atoms or hydroxy (alkyl of 1 to 4 carbon atoms), and X is oxygen or sulfur, and their non-toxic, pharmaceutically acceptable acid addition salts.

Especially preferred are 2-amino-6-ethyl-4,5,7,8-tetrahydro-6H-oxazolo[5,4-d]azepine, 2-amino-6-allyl-4,5,7,8-tetrahydro-6H-oxazolo[5,4-d]azepine, 2-amino-6-allyl-4,5,7,8-tetrahydro-6H-thiazolo[5,4-d]azepine and non-toxic, pharmaceutically acceptable acid addition salts of each.

The antianginal activity was ascertained in the following manner:

The antianginal activity of
A = 2-Amino-6-ethyl-4,5,7,8-tetrahydro-6H-oxazolo[5,4-d]azepine dihydrochloride was determined in patients with angina pectoris as follows:

METHOD

11 Patients with clinical and electrocardiographic symptoms of coronary insufficiency were selected for a crossover comparative single-blind study of compound A against placebo. Only those patients were allocated to one of the 2 treatments who complained of precordial pain at the same workload on 3 different days during the run-in period. In order to avoid carry-over effects the sequence of treatment was A placebo in every patient. 30 minutes after the injection of the test substance the patients were exercised on a bicycle ergometer. They started with a workload of 25 watts, which was increased every 3 minutes by 25 watts until the onset of pain. The heart rate and the blood pressure were registered every minute. The heart rate was determined by means of an ECG; the measurement of the blood pressure was carried out according to Riva-Rocci always by the same medical assistant.

The following parameters were evaluated:
1. Time until the onset of pain
2. Heart rate at the onset of pain
3. Blood pressure at the onset of pain
4. The workload performed, resulting from the sum of the products multiplied by the watts per minute (W×min).
5. The maximum workload, which results from the watts of the last complete exercise period (lasting 3 minutes) and the watts of the next unfinished period (watts)
6. The pressure frequency product as index for the oxygen consumption, which was calculated from the product of the heart rate and of the systolic blood pressure.

Since some patients reported pain without depression of the ST segment, ST segment was not evaluated

RESULTS

1. Duration of Exercise Performance

Under control conditions the patients could be exercised for 6 minutes on the average. After administeration of compound A the patients could be exercised 2 minutes longer.

2. Heart Rate

At the onset of pain the heart rate after administration of compound A was higher by 2 beats/min.; at the highest comparable workload the heart rate was reduced by 12 beats/min., and during the last complete minute before stopping the difference between placebo and compound A was 3 beats/min.

3. Blood Pressure

At the onset of pain the systolic blood pressure was reduced by 8 mm Hg after administration of A. The diastolic blood pressure was again unchanged. At the moment of the highest comparable workload the systolic blood pressure was reduced by 19 mm Hg after administration of A. The diastolic blood pressure was again unchanged. During the last minute before stopping the systolic blood pressure was reduced by 9 mm Hg over placebo after administration of A.

4. Work Until Workload was Stopped

The average work, which the patients performed under placebo was 495 W×min., and after administration of A 627 W×min.

5. Maximum Work

Under placebo it was 76 watts, after administration of A 87 watts.

6. Product of Pressure Frequency

Under placebo a product of pressure frequency of 310 was reached, and after administration of A at the moment of the highest comparable strain the product was 258. During the last minute before stopping this product was 313 under placebo, and 295 after administration of A.

Compound A increases the duration of exercise and exercise capacity. This is primarily due to a reduction in afterload and heartrate, expressed by decreased rate/-pressure product. It is generally agreed, that the rate pressure product is an index for oxygen consumption of the heart. Substance A therefore diminishes $O_2$ consumption, the main goal in the treatment of angina pectoris.

For that reason Compound A as well as compounds
B=2-Amino-6-allyl-4,5,7,8-tetrahydro-6H-oxoazolo[5,4-d]azepine dihydrochloride,
C=2-Amino-6-ethyl-4,5,7,8-tetrahydro-6H-thiazolo[5,4-d]azepine dihydrochloride,
D=2-Amino-6-n-propyl-4,5,7,8-tetrahydro-6H-thiazolo[5,4-d]azepine dihydrochloride,
E=2-Amino-6-allyl-4,5,7,8-tetrahydro-6H-thiazolo[5,4-d]azepine dihydrochloride,
F=2-Amino-6-(2-hydroxy-ethyl)-4,5,7,8-tetrahydro-6H-thiazolo[5,4-d]azepine dihydrochloride and
G=2-Amino-6-(4-chloro-benzyl)-4,5,7,8-tetrahydro-6H-thiazolo[5,4-d]azepine dihydrocloride
were tested as follows with regard to their heart rate lowering effect on vagotomized rats:

The animals were vagotomized and received a tracheal cannula; a polyethylene catheter was placed into the jugular vein. For measuring the ECG, needle electrodes were clamped to the extremities. During the test the body temperature of the animals was kept constant (34° C.).

After balancing out a constant starting heart rate (determined by counting the heart beats from the ECG), the test compound was intravenously administered to the animal. 30 minutes later the type was measured again.

Each compound was tested at 3 dosages administered to each of 6 animals; only one compound and dose per animal.

The average of the 6 single values per dose (Δ heart rate in beats/min.) was determined, and the dose activity curves were prepared, from which the $D_{50}$ (dose which lowers the heart rate by 50 beats/min.) was determined:

| Compound | $D_{50}$ in γ/kg i.v. |
|---|---|
| A | 500 |
| B | 100 |
| C | 32 |
| D | 12 |
| E | 42 |
| F | 37 |

-continued

| Compound | $D_{50}$ in γ/kg i.v. |
|---|---|
| G | 1400 |

Acute Toxicity

The acute toxicity was determined in mice of both sexes with an average body weight of 20 gm after administration per os. From the percentage of the animals which died within 14 days after the administration of various doses, the $LD_{50}$ was determined according to the method of Litchfield and Wilcoxon (J. Pharmacol. exp. Ther. 96, 99 (1949):

| Compound | $LD_{50}$ mg/kg p.o. |
|---|---|
| A | 2 210 |
| C | >1 500 |
| E | 455 |
| F | ~1 000 |
| G | 905 |

The preparation of the azepine drivatives of the formula I and their salts is described in the Belgian Pat. No. 771,330 and U.S. Pat. Nos. 3,804,849 and 3,907,996.

For pharmaceutical purposes the compounds of the formula I or their salts are administered to warm-blooded animals peorally, parenterally or rectally as active ingredients in customary dosage unit compositions, that is, compositions in the dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antianginal dosage unit of the compounds of the formula I or their salts is from 0.033 to 0.167 mgm/kg body weight, preferably 0.066 to 0.125 mgm/kg body weight, administered 1 to 4 times daily.

The following examples illustrate a few antianginal pharmaceutical dosage unit compositions comprising a compound of the formula I or a non-toxic acid addition salt thereof as an active ingredient and represent the best modes contemplated of carrying out the invention. The parts are parts by weight unless otherwise specified.

EXAMPLE 1

Film-coated Tablets

The tablet composition is compounded from the following ingredients:

| | |
|---|---|
| 2-Amino-6-ethyl-4,5,7,8-tetrahydro-6H-oxazolo[5,4-d]-azepine dihydrochloride | 5.0 parts |
| Lactose | 104.0 parts |
| Corn Starch | 10.0 parts |
| Magnesium stearate | 1.0 parts |
| Total | 120.0 parts |

Preparation

The ingredients are intimately admixed with each other, and the mixture is compressed at a relative humidity of less than 25% into 120 mgm-biconvex tablets which are then coated with a thin film (about 5 mgm/tablet) with the aid of a $TiO_2$-containing ethanolic hydroxypropylmethyl cellulose solution (Pharmacoat). The freshly prepared film-coated tablets are then dried in a suitable high-frequency dryer (27 or 40 MHz; 8,000 V field strength) for about 5 minutes, and finally packaged in moisture-proof packaging material.

EXAMPLE 2

Hypodermic Solution

The solution is compounded from the following ingredients:

| | |
|---|---|
| 2-Amino-6-ethyl-4,5,7,8-tetrahydro-6H-oxazolo-[5,4-d]azepine dihydrochloride | 4.0 parts |
| Lactose | 50.0 parts |
| 1 N NaOH ad pH 5.8 | . |
| Sodium chloride | 12.0 parts |
| Distilled water q.s.ad | 2000.0 parts by vol. |

Preparation

The active ingredient and the lactose are dissolved in a sufficient amount of distilled water, and the solution is adjusted to pH 5.8 with 1 N sodium hydroxide. The solution is then diluted to the indicated volume with distilled water, filtered through a membrane filter, and the filtrate is filled under aseptic conditions into cleaned and sterilized 2 cc-ampules. The contents of the ampules are then freeze-dried in conventional manner, and the ampules are sealed in a room with no more than 10% relative humidity. Reconstruction of the contents of an anpule into an injectable solution is effected by adding thereto an aqueous sodium chloride solution whose salt content is such that the reconstituted solution is blood-isotonic.

EXAMPLE 3

Suppositories

The suppository composition is compounded from the following ingredients:

| | |
|---|---|
| 2-amino-6-ethyl-4,5,7,8-tetrahydro-6H-oxazolo[5,4-d]azepine dihydrochloride | 5.0 parts |
| Suppository base (e.g. cocoa butter) | 1,695.0 parts |
| Total | 1,700.0 parts |

Preparation

The active ingredient is homogeneously stirred into the molten suppository base, and 1700 mgm-portions of the mixture are poured into cooled suppository molds and allowed to harden therein.

Any one of the other compounds embraced by formula I or a non-toxic pharmacologically acceptable acid addition salt thereof may be substituted for the particular active ingredient in Examples 1 through 3. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of treating angina pectoris in a human patient, which comprises administering to said patient an effective antianginal amount of a compound of the formula

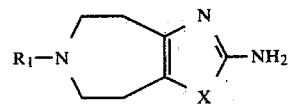

wherein
$R_1$ is hydrogen, unsubstituted or hydroxyl-substituted alkyl of 1 to 4 carbon atoms; alkyl; or unsubstituted or halo-, methyl-, methoxy- or trifluoromethyl-substituted benzyl; and X is oxygen or sulfur;
or a non-toxic, pharmaceutically acceptable acid addition salt thereof.

2. The method of claim 1, where $R_1$ is hydrogen, allyl, alkyl of 1 to 4 carbon atoms or hydroxy-(alkyl of 1 to 4 carbon atoms), and X is oxygen or sulfur.

3. The method of claim 1, where said compound is 2-amino-6-ethyl-4,5,7,8-tetrahydro-6H-oxazolo[5,4-d]azepine, 2-amino-6-allyl-4,5,7,8-tetrahydro-6H-oxazolo[5,4-d]azepine, 2-amino-6-allyl-4,5,7,8-tetrahydro-6H-thiazolo[5,4-d]azepine or a non-toxic, pharmaceutically acceptable acid addition salt of one of these.

* * * * *